(12) United States Patent
Grinberg

(10) Patent No.: US 10,716,897 B2
(45) Date of Patent: Jul. 21, 2020

(54) HYPODERMIC SYRINGE WITH VIAL ATTACHMENTS

(71) Applicant: Yair Grinberg, New Preston, CT (US)

(72) Inventor: Yair Grinberg, New Preston, CT (US)

( * ) Notice: Subject to any disclaimer, the term of this patent is extended or adjusted under 35 U.S.C. 154(b) by 0 days.

(21) Appl. No.: 15/904,771

(22) Filed: Feb. 26, 2018

(65) Prior Publication Data

US 2018/0207365 A1 Jul. 26, 2018

Related U.S. Application Data

(62) Division of application No. 12/055,075, filed on Mar. 25, 2008, now Pat. No. 9,901,682.

(Continued)

(51) Int. Cl.
*A61M 5/178* (2006.01)
*A61M 5/00* (2006.01)
(Continued)

(52) U.S. Cl.
CPC .............. *A61M 5/1782* (2013.01); *A61J 1/18* (2013.01); *A61M 5/008* (2013.01);
(Continued)

(58) Field of Classification Search
CPC .......... A61J 1/20; A61J 1/2003; A61J 1/2006; A61J 1/201; A61J 1/2013; A61J 1/2017; A61J 1/2048; A61J 1/2051; A61J 1/2055; A61J 1/2058; A61J 1/2062; A61J 1/2065; A61J 1/2068; A61J 1/2072; A61J 1/2075; A61J 1/2089; A61J 1/2096; A61M 5/178; A61M 5/1782; A61M 2005/2485; A61M 2005/2488; A61M 2005/2492; A61M 2005/2496; A61M 2005/3104; A61M 2005/3114; A61M 2005/3115; A61M 2005/3118; A61M 2005/312; A61M 5/204; A61M 5/3129; A61M 5/3134; A61M 5/3135

See application file for complete search history.

(56) References Cited

U.S. PATENT DOCUMENTS

| 657,440 A | * | 9/1900 | McCaw ................ | A61M 5/204 604/183 |
| 3,938,520 A | * | 2/1976 | Scislowicz ............ | A61J 1/2089 604/405 |

(Continued)

OTHER PUBLICATIONS

"Obstruct". Macmillan Dictionary. <http://www.macmillandictionary.com/dictionary/american/obstruct>.

*Primary Examiner* — Kami A Bosworth
(74) *Attorney, Agent, or Firm* — Ryan, Mason & Lewis, LLP

(57) ABSTRACT

A medical syringe apparatus includes a syringe unit, a hypodermic needle attached to the syringe unit and at least one interfacing member for mating a labeled medication container to the syringe unit. A filling needle is attached to the syringe unit for drawing fluid from a container. A movable needle sheath protects the hypodermic needle when not in use and may be moved out of the way when administering an injection. The medication label is visible. The container remains mated to the syringe when the syringe is in use. Risk of mislabeling the syringe may therefore be substantially reduced or eliminated and patient safety may accordingly be improved.

12 Claims, 21 Drawing Sheets

Related U.S. Application Data

(60) Provisional application No. 60/911,634, filed on Apr. 13, 2007.

(51) Int. Cl.
*A61J 1/18* (2006.01)
*A61M 5/50* (2006.01)
*A61M 5/31* (2006.01)
*A61J 1/06* (2006.01)
*A61J 1/20* (2006.01)
*A61M 5/20* (2006.01)
*A61M 5/32* (2006.01)
*A61J 1/14* (2006.01)

(52) U.S. Cl.
CPC ........ *A61M 5/3135* (2013.01); *A61M 5/5086* (2013.01); *A61J 1/065* (2013.01); *A61J 1/1406* (2013.01); *A61J 1/2037* (2015.05); *A61J 1/2062* (2015.05); *A61J 1/2075* (2015.05); *A61J 1/2082* (2015.05); *A61J 1/2096* (2013.01); *A61J 2200/10* (2013.01); *A61M 5/204* (2013.01); *A61M 5/3129* (2013.01); *A61M 5/3216* (2013.01); *A61M 5/3219* (2013.01); *A61M 2005/3104* (2013.01); *A61M 2205/585* (2013.01)

(56) References Cited

U.S. PATENT DOCUMENTS

| | | | | |
|---|---|---|---|---|
| 4,588,403 A | * | 5/1986 | Weiss | A61M 5/162 604/411 |
| 5,067,948 A | | 11/1991 | Haber et al. | |
| 5,279,576 A | * | 1/1994 | Loo | A61J 1/2096 222/1 |
| 5,334,163 A | * | 8/1994 | Sinnett | A61M 5/19 137/625.47 |
| 5,334,179 A | * | 8/1994 | Poli | A61J 1/2089 604/403 |
| 5,484,406 A | | 1/1996 | Wong et al. | |
| 5,496,288 A | * | 3/1996 | Sweeney | A61M 5/178 220/254.3 |
| 5,776,125 A | * | 7/1998 | Dudar | A61J 1/2089 604/411 |
| 5,893,842 A | | 4/1999 | Imbert | |
| 6,607,508 B2 | | 8/2003 | Knauer | |
| 6,689,108 B2 | | 2/2004 | Lavi et al. | |
| 7,056,307 B2 | | 6/2006 | Smith et al. | |
| 7,094,222 B1 | * | 8/2006 | Siekas | A61M 1/0009 604/191 |
| 7,731,678 B2 | | 6/2010 | Tennican et al. | |
| 2002/0177819 A1 | | 11/2002 | Barker et al. | |
| 2006/0287639 A1 | * | 12/2006 | Sharp | A61J 1/2096 604/415 |
| 2009/0018506 A1 | | 1/2009 | Daily et al. | |

\* cited by examiner

HYPODERMIC SYRINGE WITH VIAL ATTACHMENTS

CROSS-REFERENCE TO RELATED APPLICATION

This application is a division of U.S. patent application Ser. No. 12/055,075, filed on Mar. 25, 2008, and entitled "Hypodermic Syringe with Vial Attachment," now U.S. Pat. No. 9,901,682 issued on Feb. 27, 2018, and which claims the benefit of provisional application Ser. No. 60/911,634, filed Apr. 13, 2007, the disclosures of which are incorporated by reference herein.

BACKGROUND OF THE INVENTION

1. Technical Field

The present disclosure relates to hypodermic syringes and, more specifically, to hypodermic syringes with vial attachment(s) that allow for automatic and correct labeling of the syringes.

2. Discussion of the Related Art

In the course of administering medication to a patient by hypodermic injection, a syringe is filled from a vial of medication. While the vial is pre-labeled according to its contents, the syringe is generally unlabeled when removed from sterile wrapping. Medical practitioners such as physicians, nurses and medical technicians, may take the time to manually label a syringe after drawing medication from a vial. A syringe that is so-labeled reduces the chance of administering an incorrect medication, an occurrence that is commonly known as ampule swap error or syringe swap error.

Syringe swap error may be a particular risk in the field of anesthesiology where multiple different medications are used and a particular medication may be called upon at a moment's notice. For example, some medications must be administered in rapid succession.

Multiple medications may be drawn up in multiple syringes and labeled in the course of preparing for a surgical case, however this process may be time consuming and may itself be prone to error. In the real-world setting, medical practitioners may be unwilling and/or unable to take the time to properly label each syringe. Moreover, in manually labeling each syringe, labeling errors may occur, especially where labels are written hastily. Additionally, manually labeled syringes may not be readily legible.

Since over 5 billion injections will be given each year in the United States and practitioners can make mistakes such as mislabeling syringes during a certain fraction of those injections, the potential for complications related to syringe mislabeling is large. For example, it is estimated that there is some type of medication administration error for every 130 anesthetics administered. Moreover, it is highly likely that medication errors are underreported.

Manual labeling may give rise to other potential problems, for example, the type of medication may be labeled but other information such as the concentration, the inactive ingredients, and the expiration date may be omitted. Such information may even be intentionally omitted from the syringe labels but may later be needed in order to quickly determine the cause of a problem in the event of complications, at which point, the vial may have since been deposited in a sharps container and may be irretrievable.

Labels may be preprinted in an attempt to minimize some of the problems discussed above; however, preprinted labels may be mistakenly applied to the wrong syringe. Moreover, the use of adhesive labels may be problematic when working with gloved hands, as is generally the case in operating rooms.

Syringes may be pre-labeled at the time of assembly; however, pre-labeled syringes are significantly less versatile as a syringe pre-labeled for one medication may not be used to administer another medication. Accordingly, hospitals and other medical facilities must stock enough syringes for each type of medication used. Accordingly, the costs of procuring, storing and retrieving the correct pre-labeled syringe may be inordinately expensive. Moreover, the incorrect pre-labeled syringe may be inadvertently used.

Labeled syringes can be pre-filled with medication at the factory. Such pre-filled syringes are available for some medications, but are cumbersome in that they need to be assembled with special injectors prior to use. This re-assembly adds time to procedure setup. In addition, drugs packaged this way are more expensive to produce and require more storage space than drugs packaged in traditional vials and ampules. For this reason the cheaper and more space efficient vials and ampules continue to be used in most hospitals.

Significant advances have been made in industrial quality control when it comes to labeling medications at the factories where they are produced. Although each year, billions of medication vials, ampules and bottles are produced, there are no recalls issued for inaccurate or incomplete labeling. Separation of assembly lines, chemical analyses and other quality control measures have reduced the possibility of a miss-labeled medication container.

However, when a disposable syringe is used to draw up and administer a medication in clinical practice, labeling the syringe depends on thoughtful input from a medical practitioner such as a physician or nurse.

SUMMARY

Embodiments of the present invention provide a syringe that can be reliably labeled each time a medication is transferred to the syringe so that contents of the syringe can be correctly labeled, essentially independent of or independent of practitioner thought or attention.

A medical syringe apparatus includes a syringe unit. A filling needle is attached to the syringe unit for drawing fluid from a container. A hypodermic needle is attached to the syringe unit for injecting the fluid drawn from the container. The filling needle and the hypodermic needle are two distinct needles.

A medical syringe apparatus includes a syringe unit. A hypodermic needle is attached to the syringe unit for injecting the fluid drawn into the syringe unit. A needle sheath protects the hypodermic needle. The needle sheath is rotatably connected to the syringe unit such that the needle sheath reveals the hypodermic needle when force is provided and conceals the hypodermic needle when force is discontinued.

A method for administering a hypodermic injection includes applying force to a needle sheath to move the needle sheath and reveal a hypodermic needle. The hypodermic injection is administered while the needle sheath is in the moved position. Force is discontinued to return the needle sheath to its original position and to conceal the hypodermic needle.

BRIEF DESCRIPTION OF THE DRAWINGS

A more complete appreciation of the present disclosure and many of the attendant advantages thereof will be readily obtained as the same becomes better understood by reference to the following detailed description when considered in connection with the accompanying drawings, wherein.

DETAILED DESCRIPTION OF EXEMPLARY EMBODIMENTS

Figure 1:
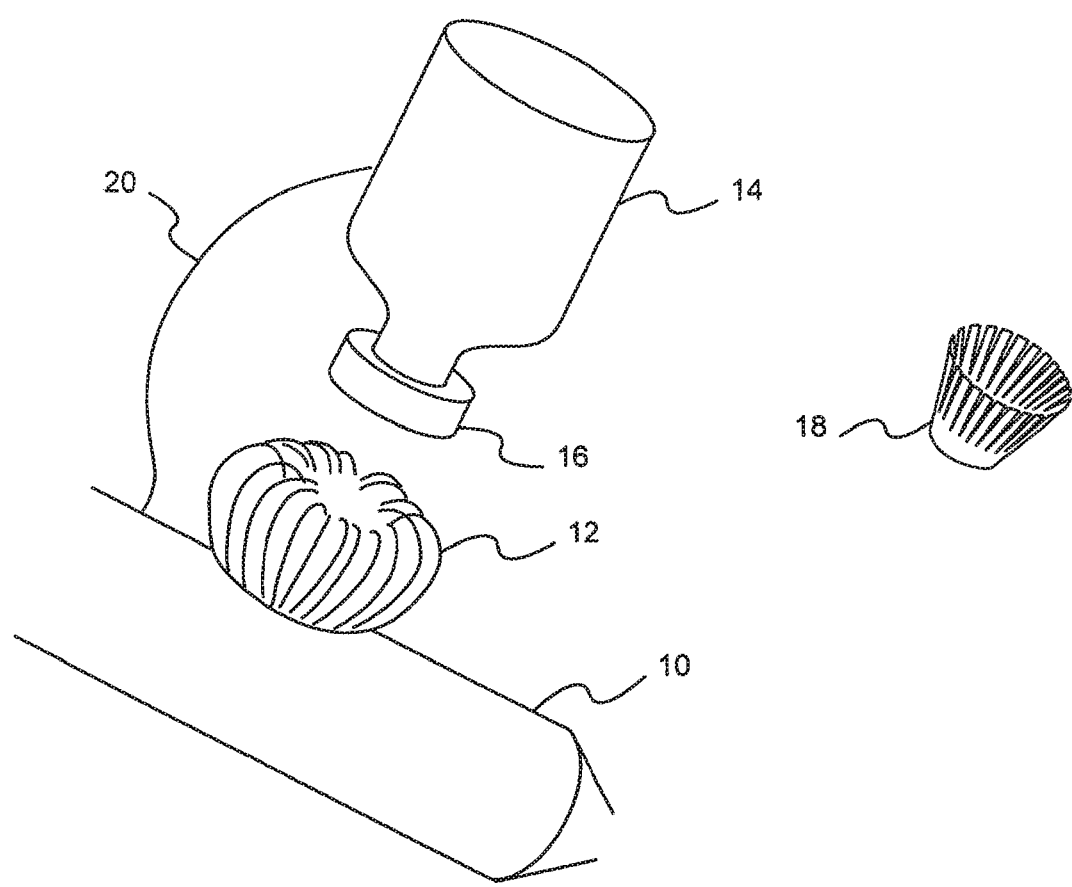
FIG. 1 illustrates a syringe capable of mating with a medicine container according to an exemplary embodiment of the present invention.

In describing the exemplary embodiments of the present disclosure illustrated in the drawings, specific terminology is employed for sake of clarity. However, the present disclosure is not intended to be limited to the specific terminology so selected, and it is to be understood that each specific element includes all technical equivalents which operate in a similar manner.

Exemplary embodiments of the present invention relate to a syringe, for example, a hypodermic syringe, which may be mated to a medication container, for example, an ampule or vial. After drawing medication from the vial into the syringe, the medical practitioner may mate the used vial to the syringe. By mating the medication vial to the syringe, medical practitioners may be able to easily determine the contents of the syringe by reading the label on the medication vial.

According to some exemplary embodiments of the present invention, the vial may be mated to the syringe by an interfacing member incorporated with the syringe. The interfacing member may lock the vial in place using friction forces and/or an adhesive coating. The interfacing member may be able to accommodate vials of various body and neck sizes by flexing, bending and/or choking down on the vial. In some exemplary embodiments, the vial may be permanently affixed to the syringe. In other exemplary embodiments, the vial may be removably affixed to the syringe, for example, to allow for additional medication to be drawn from the vial at a latter point and to allow for subsequent reattachment of the vial to the syringe. Where the vial is removably affixed, a tethering connector may be used to ensure physical proximity and to minimize the risk of the wrong vial being affixed to the syringe.

A user, for example a medical practitioner, may mate the vial to the syringe after drawing medication from the vial into the syringe. After the medication has been drawn, the user may be holding the syringe in one hand and the vial in the other hand. Accordingly, the vial may be quickly and easily mated to the interfacing member of the syringe after the medication has been drawn. Where multiple syringes are used to draw medication from multiple corresponding vials, the user may easily draw medication and mate the corresponding vial to the syringe before the syringe and vial are put down. Accordingly, multiple medications may be drawn into multiple corresponding syringes and the syringes may be labeled by mating the corresponding vial to the corresponding syringe with little to no risk of label confusion.

Exemplary embodiments of the present invention contemplate various interfacing members including snapping locks, clamping locks, tying locks, ratchet locks, twist locks, buckle locks, adhesive pads, and the like. According to some exemplary embodiments, a single syringe may include multiple interfacing members for holding multiple vials simultaneously, where a single syringe contains multiple medications. Alternatively, the multiple interfacing members may be used to hold a single vial and the multiple interfacing members are each suitable for mating a vial of a different size and/or shape.

The figures and the disclosure below describe various exemplary embodiments of the present invention having various features. It should be understood that the features described with respect to one exemplary embodiment may be combined with features described with respect to other exemplary embodiments.

FIG. 1 illustrates a syringe capable of mating with a medicine container according to an exemplary embodiment of the present invention. In FIG. 1, the syringe 10 may have an interfacing member for mating a medication vial 14 to the syringe 10. The interfacing member may be, for example, a clamping unit 12. The clamping unit 12 may include a material that can flex and exert a restoring force, for example, a plastic or a shape memory alloy. Accordingly, a portion of the vial 14, for example a cap 16 of the vial 14, may be inserted into the clamping unit 12 and may be held in place by friction forces. The clamping unit 12 may be arranged to allow for the vial 14 cap 16 to be inserted and to prevent easy removal. This may be accomplished, for example, by including a plurality of flexors that are bent inwards, as shown. Alternatively, the interfacing member may be a clamping unit 18 including a plurality of flexors that are not bent inwards so that insertion, removal and reinsertion may be more easily accommodated.

In some exemplary embodiments of the present invention, a tether 20 is provided to link the syringe 10 to the vial 14, even when the vial 14 is not mated. The tether 20 may be a flexible material such as plastic, latex, string, wire or the like. The tether 20 may attach to the vial by, for example, an adhesive measure or by friction. For example, the tether 20 may have a rubber band loop for holding the vial 14. Alternatively, the tether 20 may include a plastic tie-wrap, also known as a zip tie, for holding the vial 14. The tether 20 may secure the vial at its body, as shown, or the tether 20 may secure the vial at its neck.

Alternatively, the vial 14 may be glued, taped, snapped or screwed to the syringe 10. In such exemplary embodiments, the interfacing member may be the selected adhesive mechanism. The interfacing member may be attached to the syringe 10 during manufacture; alternatively, the interfacing member may be formed as part of the syringe 10, for example, during an injection molding process, extrusion process or some other manufacturing process.

According to an exemplary embodiment of the present invention, the interfacing member may be an adhesive pad attached to the syringe 10. The adhesive can be on the body or plunger of the syringe itself and/or covering an adhesive cup. The adhesive pad may be covered with a protective film that may be easily removed when coupling to a vial is desired.

Figure 2:
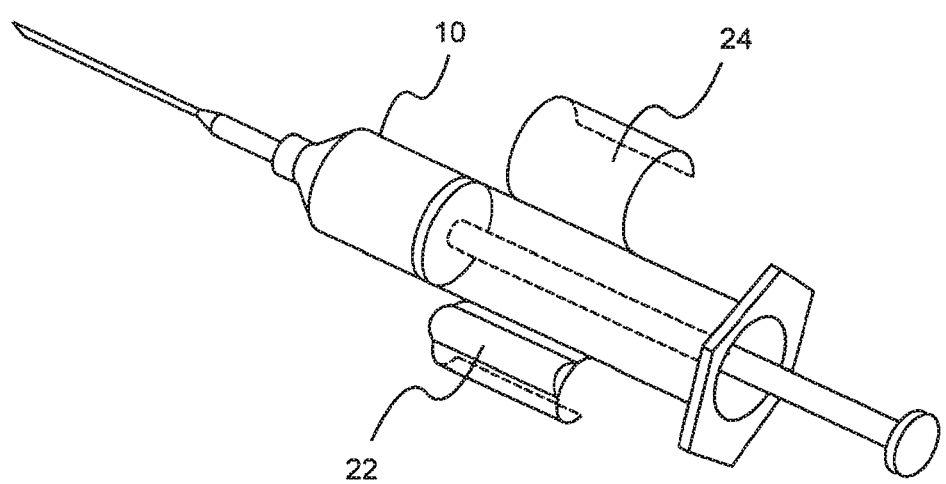
FIG. 2 illustrates a syringe having multiple interfacing members for mating with medicine containers of various sizes according to an exemplary embodiment of the present invention.

As discussed above, exemplary embodiments of the present invention may have multiple interfacing members for mating either multiple medication containers at the same time or for mating one of a variety of differently sized containers. FIG. 2 illustrates a syringe having multiple interfacing members for mating with medicine containers of various sizes according to an exemplary embodiment of the present invention. In FIG. 2, the syringe 10 includes a first interfacing member 22 and a second interfacing member 24. While some exemplary embodiments of the present invention may have multiple interfacing members of the same size, FIG. 2 shows an exemplary embodiment having multiple interfacing members of differing sizes. While some exemplary embodiments may have one, two, three or more interfacing members, FIG. 2 shows an exemplary embodiment having two interfacing members.

The first interfacing member 22 may be a small-sized interfacing member for mating to small ampules or vials. The second interfacing member 24 may be a large-sized interfacing member for mating to large ampules or vials. The interfacing members 22 and 24 shown in FIG. 2 are examples of clasps that grab and hold medicine containers by either squeezing tightly around the perimeter of the vial or by adhering to the surface of the vial; however, multiple interfacing members may be of other forms as well.

Rather than having multiple interfacing members for holding containers of various sizes, a single adjustable interfacing member may be used. For example, the interfacing member could be a spiral shaped arm of plastic or memory alloy that may flex to accommodate containers of various sizes. Alternatively or additionally, a ratcheting zip tie or ratchet tie can be used to bind vials of various sizes.

Figure 3:
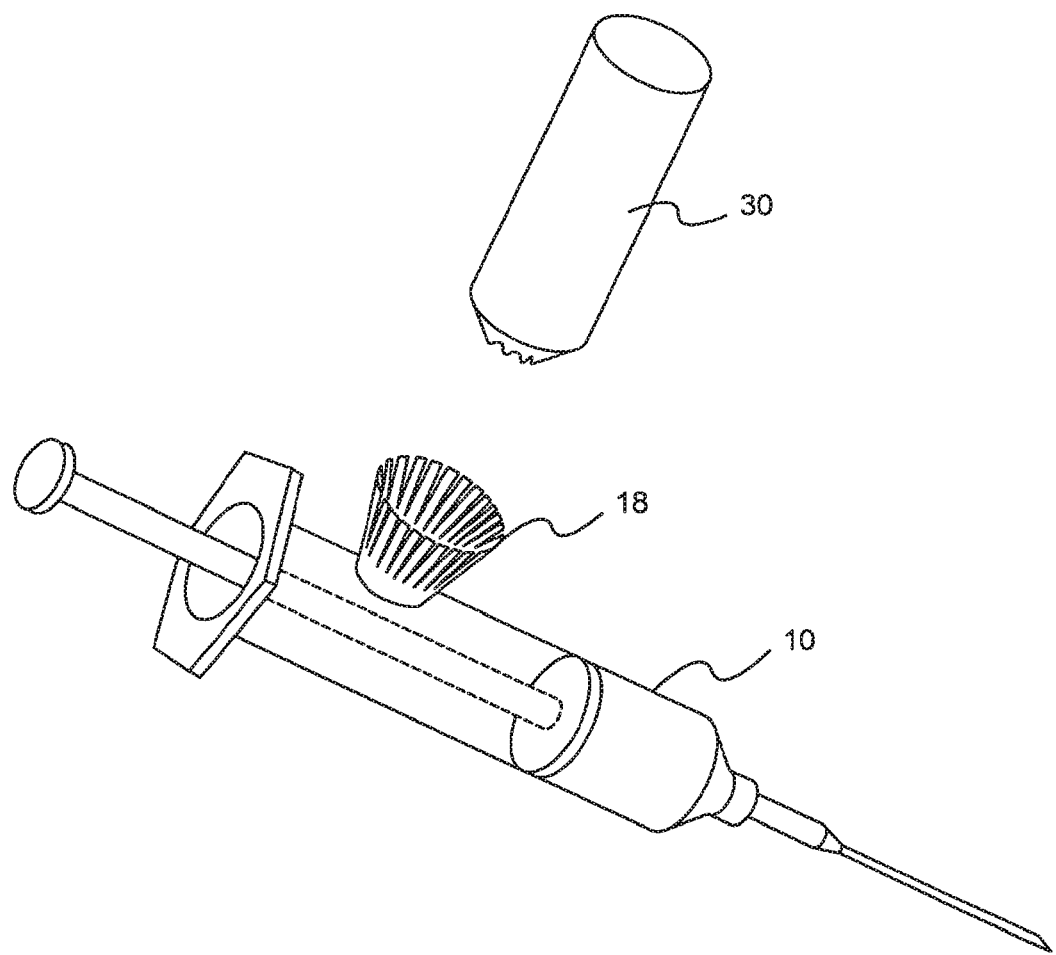
FIG. 3 illustrates a syringe capable of mating with a medicine container, for example, an ampule 30 with a sharp end, while protecting the medical practitioner from risk of accidental contact with the sharp end, according to an exemplary embodiment of the present invention.

Ampules are containers of medication that may be broken open. Accordingly, after having been opened, ampules may have a sharp end of broken glass. Exemplary embodiments of the present invention may mate with open ampules in such a way as to protect the medical practitioner from risk of accidental contact with the sharp end of open ampules. FIG. 3 illustrates a syringe capable of mating with a medicine container, for example, an ampule 30 with a sharp end, while protecting the medical practitioner from risk of accidental contact with the sharp end, according to an exemplary embodiment of the present invention. As seen in FIG. 3, the syringe has a clamping unit 18 as an interfacing member. The clamping unit 18 may conceal the sharp end of the ampule 30 after it is snapped in place.

Figure 4:
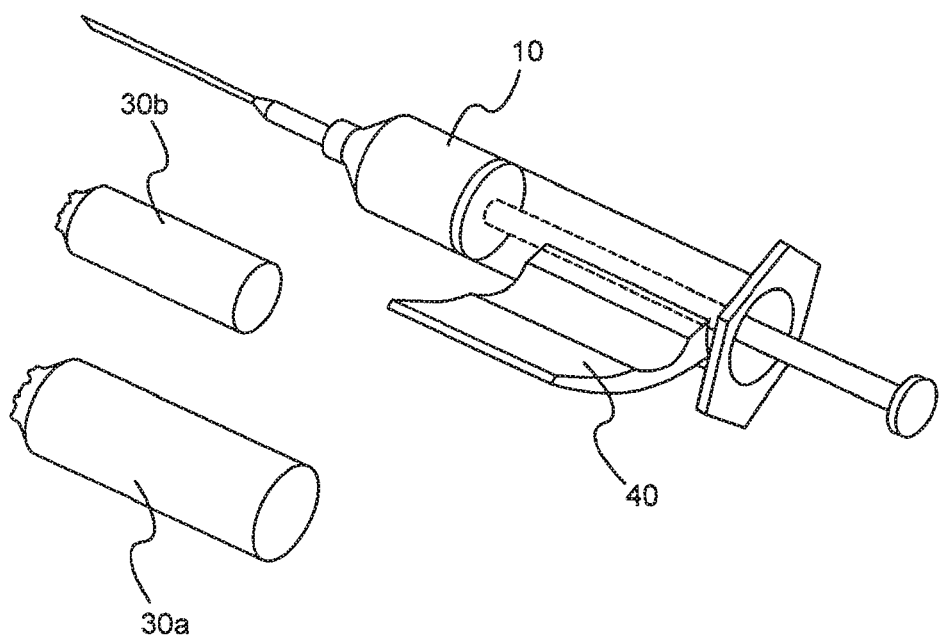
FIG. 4 illustrates a syringe including an adhesive cup as an interfacing member according to an exemplary embodiment of the present invention.

According to another exemplary embodiment of the present invention illustrated in FIG. 4, the syringe 10 may include an adhesive cup 40 as an interfacing member. The adhesive cup 40 may have a concave surface to receive the container. The adhesive cup 40 may be flexible to allow for a tail end of the adhesive cup to wrap around the vial for additional adhesive contact.

A sterile packaging may cover the bonding adhesive to facilitate rapid bonding of the vial to the syringe, since removing the wrapper automatically exposes the adhesive. Quick labeling may then be performed with little to no opportunity for labeling error as the vial travels from the hand that held it while medication was being drawn up directly to the adhesive pad.

The adhesive cup 40 may be made of a soft plastic and/or foam or otherwise deformable material and may be able to bond to vials of different diameters by accommodating a desired radius of curvature. The adhesive cup may be mounted on an extension that protrudes from the syringe or the adhesive cup may be mounted directly to the syringe.

Alternatively, the adhesive cup 40 may be rigid. The adhesive cup 40 may comprise a contoured arm covered by adhesive glue for mating with the container. The adhesive cup 40 may be strongly adhesive to prevent removal of the container or may be less-strongly adhesive to allow for removal and replacement of the container.

Alternatively, a removably adhesive device, for example, VELCRO fabric hook-and-loop fastener strips, may be provided on the adhesive cup 40. For example, a first VELCRO fabric hook-and-loop fastener strip may be provided upon the adhesive cup 40 and a second VELCRO fabric hook-and-loop fastener strip that is capable of mating with the first VELCRO fabric hook-and-loop fastener strip may be provided, in a mated state, upon the first VELCRO fabric hook-and-loop fastener strip. The second VELCRO fabric hook-and-loop fastener strip may then have an adhesive surface for mating with the container. Accordingly, a container mated with the adhesive surface may be freely removable from the adhesive cup 40 and replaceable by virtue of the VELCRO fabric hook-and-loop fastener strip. Alternatively, the first VELCRO fabric hook-and-loop fastener strip may be provided directly on the body of the syringe instead of on the adhesive cup 40.

In such embodiments, VELCRO fabric hook-and-loop fastener is mentioned as an example of a suitable reatachable fastener, however, other mating fasteners such as snaps and magnetic devices may be used.

The adhesive surface of the adhesive cup 40 or second VELCRO fabric hook-and-loop fastener strip may be covered by a protective film to protect the adhesive surface when contained in its sterile packaging. The concave surface may have an irregular concavity to allow for the holding of different sized containers, for example, a large ampule 30a or a small ampule 30b. For example, the concavity may have a large radius at one end and have a small radius at the other end. Flexibility may also facilitate the holding of different sized containers.

Figure 5:
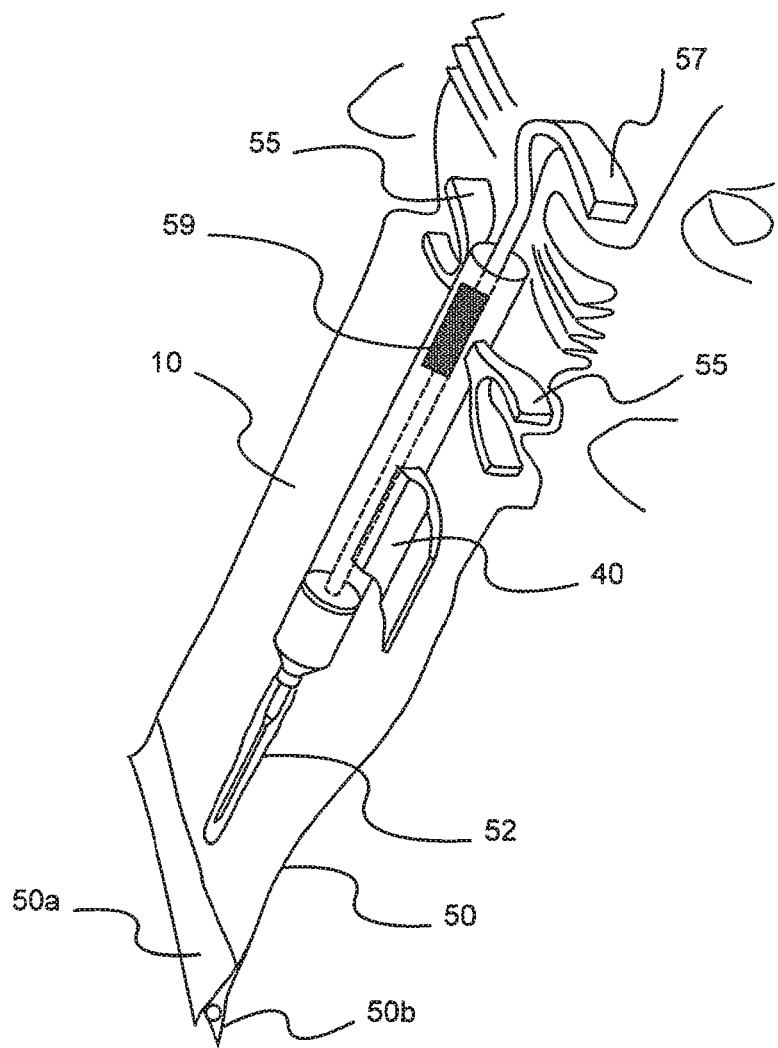
FIG. 5 illustrates a syringe capable of mating with a medicine container according to an exemplary embodiment of the present invention.

For exemplary embodiments having an adhesive surface, either directly on the adhesive cup 40 or on a second VELCRO fabric hook-and-loop fastener strip, the protective film that protects the adhesive surface may be coupled to the sterile packaging of the syringe such that when the sterile packaging is removed, so too is the protective film. For example, the protective film may be attached to the sterile packaging or, for example, the sterile packaging may itself protect the adhesive surface. FIG. 5 illustrates a syringe capable of mating with a medicine container according to an exemplary embodiment of the present invention. In FIG. 5, the syringe is packaged in a sterile packaging 50. The sterile packaging 50 may be, for example, a two-layer peel pack including an upper layer 50a and a lower layer 50b. The upper layer 50a may be transparent; the lower layer 50b may be shrink-wrapped around the flanges 55 of the syringe 10. The syringe 10 may include an adhesive cup 40 with an adhesive top surface. A layer of the sterile packaging 50, for example, the upper layer 50a may be pressed against the adhesive top surface of the adhesive cup 40.

When opening the sterile packaging 50, the medical practitioner may grip the syringe 10 in the sterile packaging 50 in the vicinity of the flanges 55 and a hook-end 57 while a needle-end 52 of the syringe 10 is unpackaged. The medication may then be drawn from a vial prior to unpackaging the remainder of the syringe 10. When the remainder of the syringe 10 is unpackaged, the upper layer 50a may be pulled from the adhesive cup 40 thus exposing the adhesive top surface. The vial of medication used to fill the syringe may then be adhered to the adhesive cup 40, for example, in the manner discussed above. As discussed above, the adhesive cup 40 may utilize a permanent adhesive for irremovably attaching the vial to the adhesive cup 40 or a milder adhesive may be used for removably attaching the vial to the adhesive cup 40. Embodiments allowing for removal may incorporate the use of a tether for maintaining a link between the vial and the syringe even when the vial is in a removed state.

The syringe 10 illustrated in FIG. 5 may be used in a different way. When opening the sterile packaging 50, the medical practitioner may grip the syringe 10 in the sterile packaging 50 in the vicinity of the flanges 55 and a hook-end 57 while a needle-end 52 of the syringe 10 is unpackaged. The medication may then be drawn from a vial prior to unpackaging the remainder of the syringe 10. The now filled syringe may be further unpacked and dropped onto a surgical sterile field. When used in this way the time required to draw up medication into a sterile syringe on a sterile surgical field may be decreased as compared to the traditional method of pouring the medication into a sterile cup and having a scrub nurse draw the medication into the syringe. By extending a long tether from the syringe off of the field and connecting it to the vial, the vial can still serve as the label. Alternatively, the vial can be dropped into a sterile plastic bag, which may then be attached to the syringe as previously described. Accordingly, the syringe may be filled prior to being placed on a sterile field without compromising its sterility. This feature may be implemented either separately from or in addition to the features discussed herein relating to correctly labeling syringes. In another alternative, the syringe can be packaged with a sterile pen and labeled in the traditional way by writing the name of the mediation on the adhesive plate after the loaded, but still sterile syringe is dropped out of the packaging and on to the sterile field.

The syringe 10 may also include an indicator pad 59 which may act as a timer to indicate the time which has elapsed since opening the package or since filling the syringe. The act of tearing apart the peal packing can act as a trigger which begins the process of timing. Furthermore, such a device can be used on all medical supplies which come in sterile packaging and must be unpacked prior to use. The indicator pad 59 may be used to indicate whether the sterile packaging 50 has been opened and/or for how long the packaging 50 has been opened. According to one exemplary embodiment of the present invention, the indicator pad 59 is capable of changing color when removed from the packaging 50. For example, the indicator pad 59 may include a color-change dye that changes from one color to another color when exposed to ambient air and/or ambient light. For example, the color-change dye may change color to reflect oxidation as the dye is exposed to oxygen in the atmosphere. In such a case, the sterile packaging 50 may be packaged in an oxygen-free environment, such as a vacuum or an environment filled with an inert gas such as nitrogen.

Alternatively, the color-change dye may change color when exposed to ambient light. In such a case, an opaque covering may conceal the indicator pad 59 while the syringe 10 is packaged. When the syringe 10 is removed from the wrapper, the opaque covering may be simultaneously removed. For example, the opaque covering may be part of or otherwise coupled to the packaging 50. The opaque covering may also be, or may alternatively be a gas-impermeable protective covering that protects the indicator pad 59 from exposure to the air within the packaging 50. This may allow the syringe to be packed in an oxygen environment without initiating color change in the indicator pad 59.

The indicator pad may include a chamber of disappearing ink or a similar substance which may be opened when the syringe is unwrapped, for example, by ripping the ink's container and allowing it to stain a piece of blotter paper. Photochrome ink, which disappears after 24 hours, can be used for this purpose. When the blotter paper is clear, the syringe has been opened for more than 24 hours and should not be used. These types of timing devices can work through photochemical mechanisms, such as previously described, or through a mechanical and/or electronic device. For example, opening the package may free up a spring in the side of the syringe which acts as a mainspring to start a disposable watch.

In another example, the syringe can have thin coatings of differently charged materials separated by a thin insulator but connected to an electrochemical watch by wires. Pulling apart the materials may then cause a momentary current flow which is enough to start the electrochemical watch. Alternatively, other methods for implementing a timer that either counts the time that has elapsed since the package has been opened and/or counts down the time for which the syringe remains viable may be used. Such other methods as not herein disclosed may be understood by those of ordinary skill in the art, and are presumed to be within the scope of the exemplary embodiments of the present invention.

Alternatively the act of filling the syringe may initiate a timer method, for example, it may cause a region of the syringe to begin to fill with the syringe contents, for example by a capillary action, which may then lead to a visible change in the syringe after a set amount of time.

In yet another example of timing how long a syringe has been open, each syringe may be manufactured with a unique machine-readable indicator such as a bar coded serial number. In environments where bar code scanning is used to confirm medication identity from the vial's bar code, the syringe number can be scanned as well and a computer can keep track of the time when any syringe was filled and what medication actually entered the syringe. If problems occur, they may be tracked back to the lot of the drug and to the syringe itself.

The indicator pad 59 may have a single color change state that is initiated during a single exposure to ambient conditions. In such a case, the indicator pad 59 indicates whether the packaging has been opened. Alternatively, the indicator pad 59 may have multiple color change states, or may otherwise continuously change as ambient exposure increases. In such a case, the length of time the syringe 10 has been unpackaged for may be readily determined by examining the state of the indicator pad 59.

The indicator pad 59 may change color in a single section or may include multiple sections that change color at different exposure durations. Each section may be a geometric shape or may form lettering and/or numbering that helps to communicate the state of the indicator pad 59. Additional lettering and instructions may be printed on the syringe 10 to help the user interpret the color change.

Figure 6:
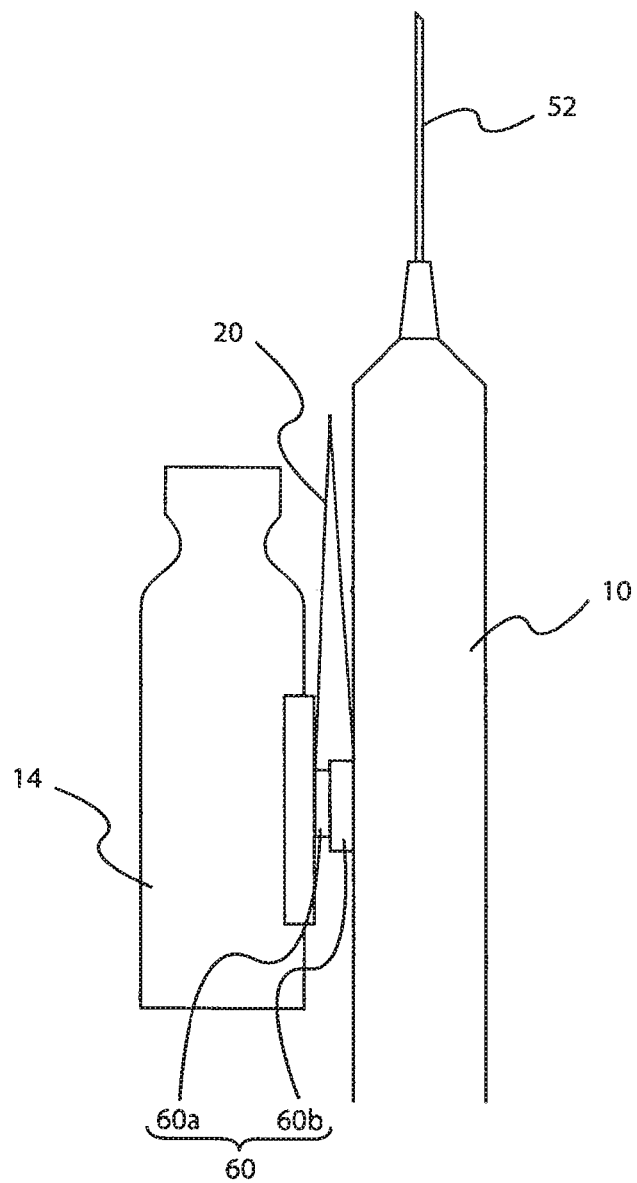
FIG. 6 illustrates a syringe attached to a vial via a locking member according to an exemplary embodiment of the present invention.

FIG. 6 shows a syringe 10 attached to a vial 14 via a locking member 60 according to an exemplary embodiment of the present invention. The locking member includes an upper-portion 60a that may be attached to the vial, for example, by an adhesive, and a lower-portion 60b that may be attached to the syringe. The upper-portion 60a and the lower portion 60b removably interlock, for example, by snapping, adhesiveness and/or by magnetic members. A tether 20 may connect the syringe 10 and the vial 14 even when the vial 14 is detached. The tether 20 may be connected, at one end, either to the syringe 10 or to the lower-portion 60b of the locking member 60. The tether 20 may be connected, at the other end, to the upper-portion 60a of the locking member 60. By connecting the tether 20 to the upper-portion 60a, the medical practitioner does not have to affix the tether 20 to the vial 14. The tether 20 may be long enough to allow the needle 52 to be inserted into the vial 14 during filling. In some embodiments of the device the tether itself may be the transfer tube by which the medication fills the syringe, while in others the tether is separate form the filling tube.

Figure 7:
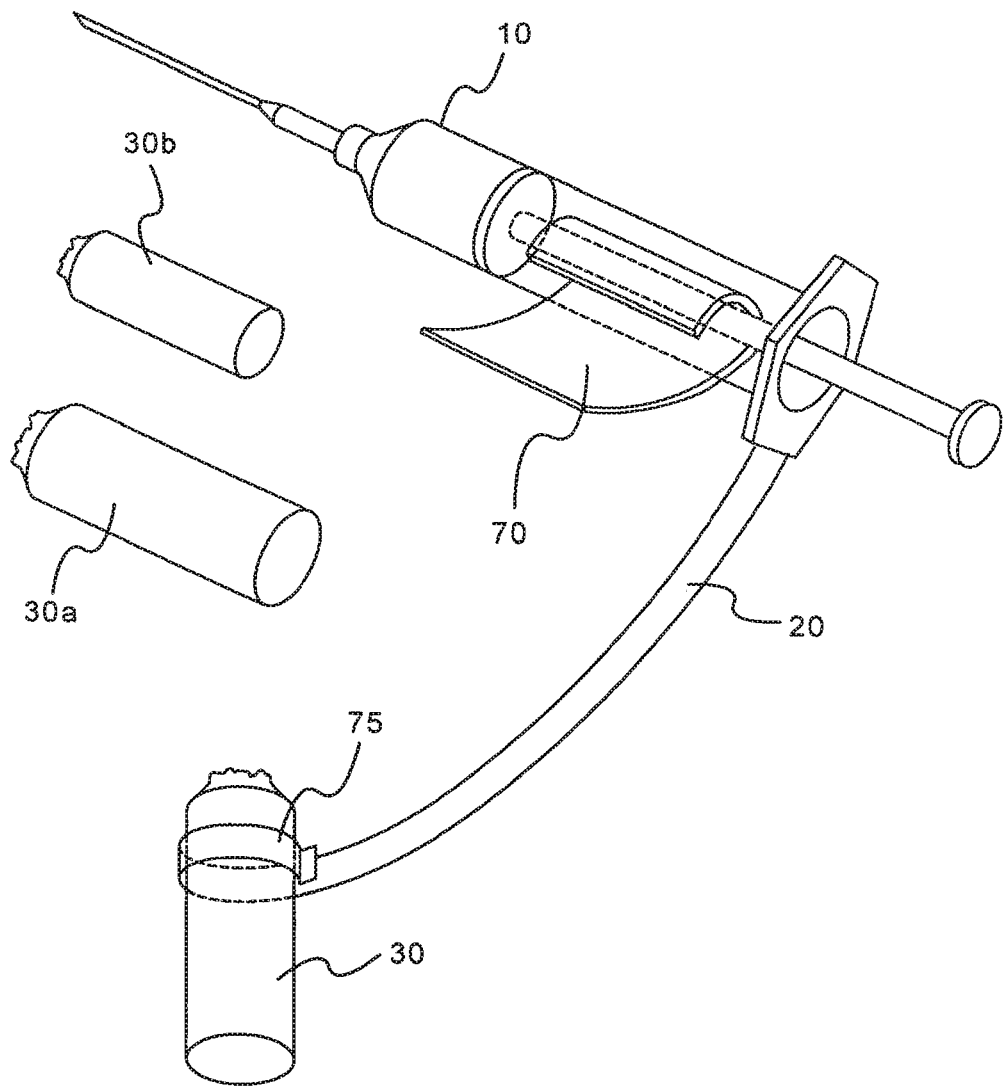
FIG. 7 illustrates a tether connecting a syringe with a container according to an exemplary embodiment of the present invention.

According to an exemplary embodiment of the present invention shown in FIG. 7, the tether 20 may include a band that connects to the syringe 10 at one end and terminates in a loop 75 at the other end. The loop 75 may close upon the container 30, for example, by including a zip-tie. The loop 75 may be adjustable to accommodate containers 30 of various sizes, for example, a small container 30b or a large container 30a. The interfacing member may be a fastening loop 70 that may either adhere to the container 30 and/or lock around the container 30. The fastening loop may be flexible and may thus accommodate containers of various sizes.

The syringe may also be configured to count the number of vials that have been attached and then removed. This may be accomplished, for example, by utilizing a multi-layered adhesive surface on the adhesive cup such that every time a vial is removed from the adhesive cup, the vial takes with it one of the adhesive layers. The number of vials removed from the syringe may then be determined from the number of layers that have been removed from the adhesive cup. Each layer may be numbered such that the number clearly indicates to the medical practitioner how many layers have been removed, and thus, how many vials have been attached to the adhesive cup. To prevent more than one such layer from being removed with a single vial, the various layers may be adhered to differing degrees or another method known in the art may be used. This feature may be especially useful where multiple vials of medication are used with a single syringe.

Figure 8:
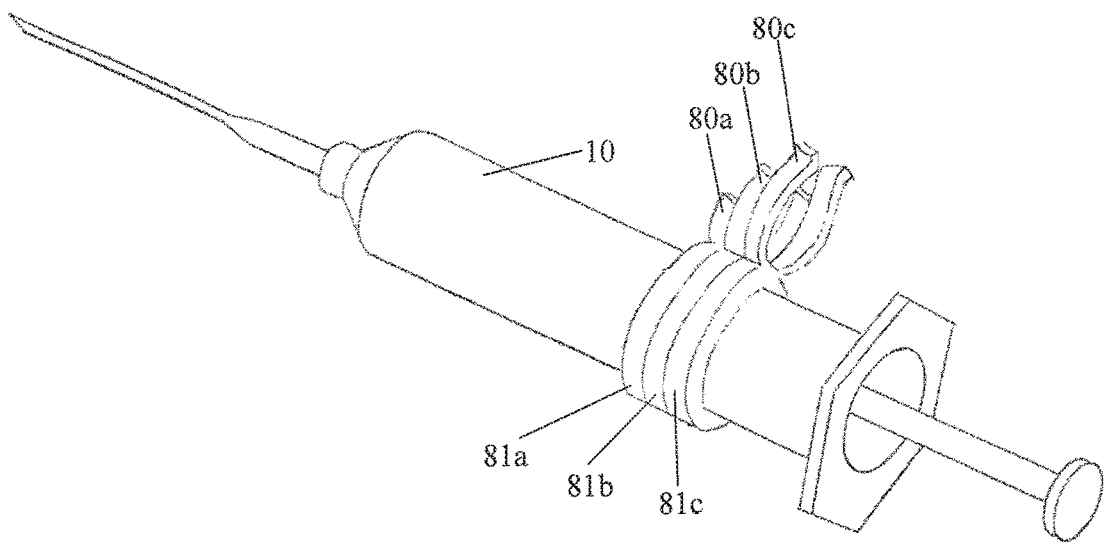
FIG. 8 illustrates a syringe including multiple interfacing members according to an exemplary embodiment of the present invention.

Exemplary embodiments of the present invention may utilize any number of interfacing members. FIG. 8 shows a syringe including multiple interfacing members according to an exemplary embodiment of the present invention. As shown in FIG. 8, the syringe 10 may include multiple interfacing members 80a, 80b, and 80c of differing sizes so that variously sized containers may be properly accommodated. The interfacing members 80a, 80b, and 80c may each rotate so that the unused interfacing members may be rotated so as not to obstruct the placement of the vial. Each of the interfacing members shown in this figure are horseshoe shaped and at least somewhat flexible to allow for a cylindrical vial to snap into place; however, other designs are possible. The interfacing members 80a, 80b, and 80c are each attached to corresponding rings 81a, 81b, and 81c and are thus free to rotate about the syringe 10 shaft.

Figure 9:
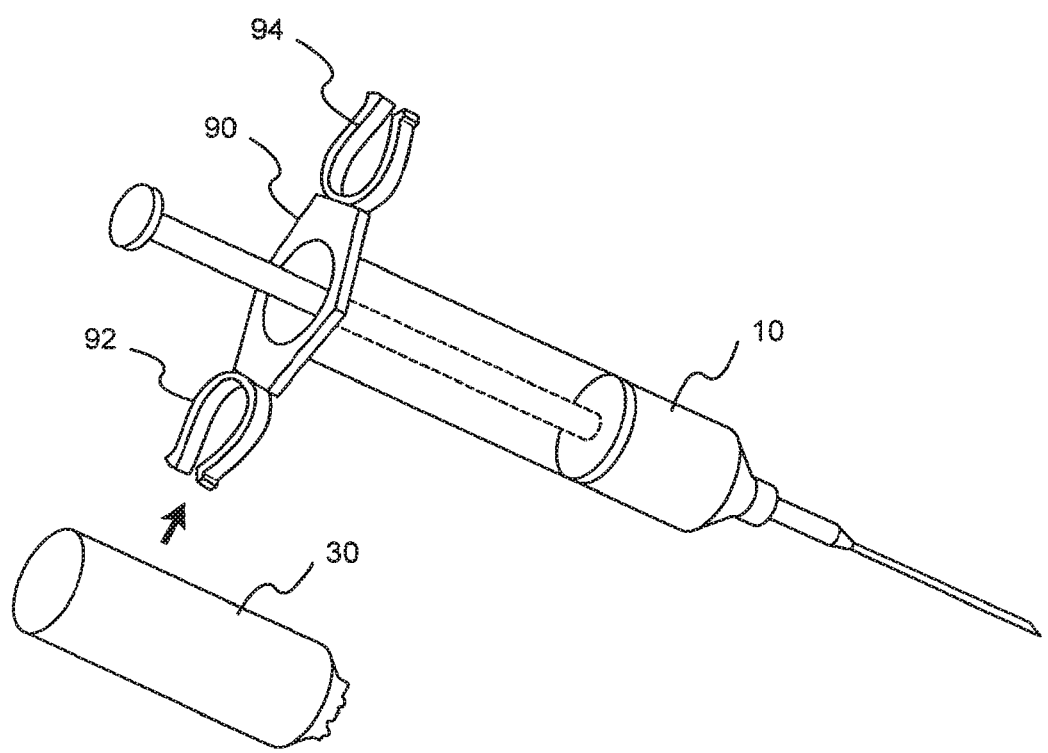
FIG. 9 illustrates a syringe with integrated interfacing members according to an exemplary embodiment of the present invention.

As shown in FIG. 8, the interfacing members may be formed of parts that are added to the syringe apparatus during assembly. Alternatively, the interfacing members may be manufactured as part of the syringe. FIG. 9 shows a syringe with integrated interfacing members according to an exemplary embodiment of the present invention. In FIG. 9, the interfacing members include a first interfacing member 92 and a second interfacing member 94 that are each formed as part of the syringe 10 flange 90. Each interfacing member 92 and 94 are shown as being horseshoe shaped, however other configurations are contemplated. Two interfacing members are shown, however, there may be any number of interfacing members, for example, there may be one, two, three, or four interfacing members. Each of the interfacing members may be configured to accommodate a container 30 of a different size. For example, interfacing member 92 may accommodate a smaller container while interfacing member 94 may accommodate a larger container.

Figure 10:
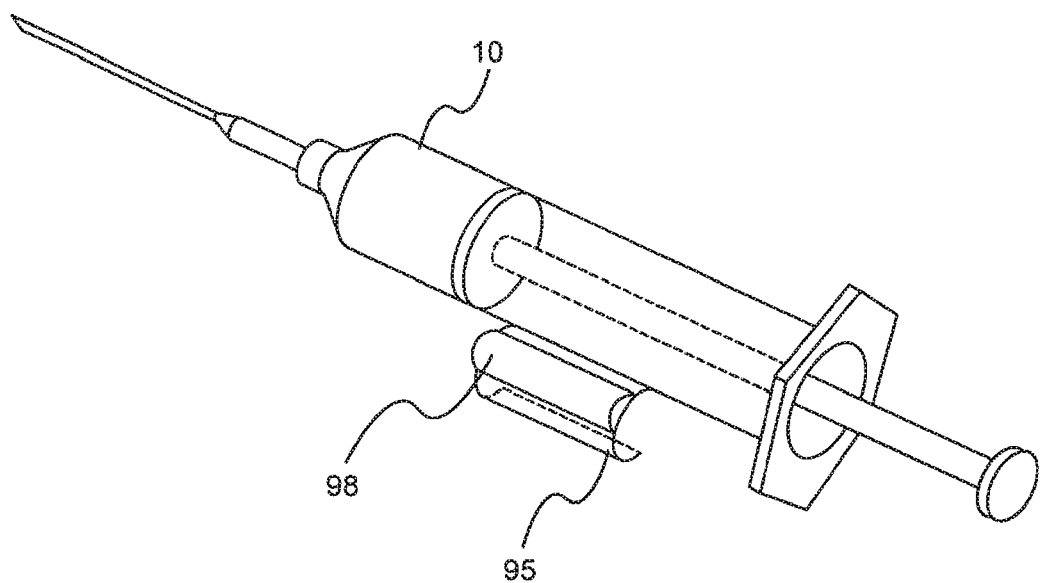
FIG. 10 illustrates a syringe including an interfacing member for mating a container of medication where the interfacing member includes a magnifying member for magnifying a label of the container of medication according to an exemplary embodiment of the present invention.

FIG. 10 illustrates a syringe including an interfacing member for mating a container of medication where the interfacing member includes a magnifying member for magnifying a label of the container of medication according to an exemplary embodiment of the present invention. Here, the syringe 10 may include an interfacing member 95, for example, as described above. However, the interfacing member 95 may additionally include a magnifying member 98, which may be, for example, a lens. The magnifying member 98 may magnify text of the container label and thus may make the contents of the container more easily read by the medical practitioner.

Figure 11A:
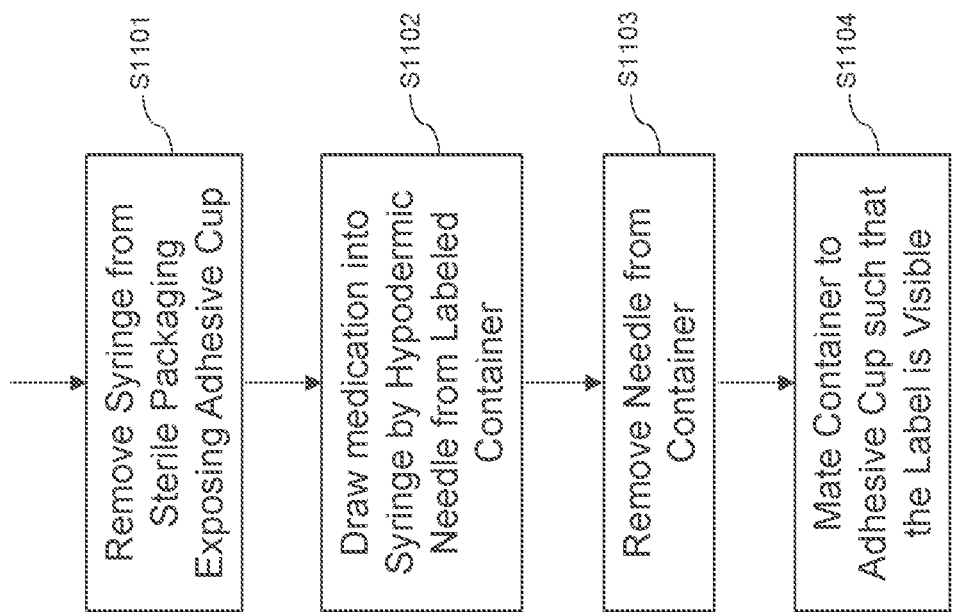
FIG. 11A illustrates a method for labeling a syringe according to an exemplary embodiment of the present invention.

FIG. 11A illustrates a method for labeling a syringe according to an exemplary embodiment of the present invention. Where the syringe is packaged in a sterile packaging as described above and illustrated in FIG. 5, the syringe may be removed from the sterile packaging (Step S1101). As described above, as the packaging is removed, an adhesive surface of an interfacing member, for example, an adhesive cup, may become exposed. A hypodermic needle attached to the syringe may be inserted into a labeled container of medication and medication may be drawn into the syringe (Step S1102). The needle may then be removed from the container (Step S1103) and the container may be mated to the interfacing member (Step S1104). The interfacing of the container to the interfacing member may include, for example, attaching the container to the adhesive cup, where the interfacing member is an adhesive cup.

Figure 11B:
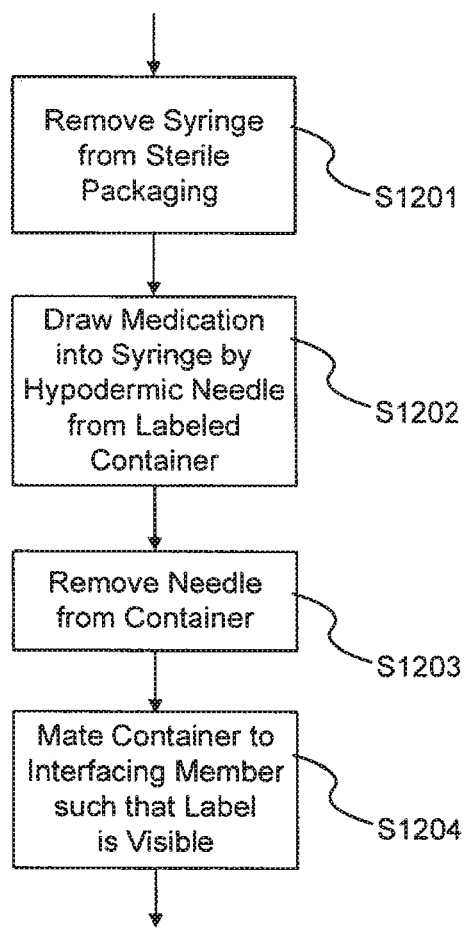
FIG. 11B illustrates another method for labeling a syringe according to an exemplary embodiment of the present invention.

Alternatively, it is to be understood that the interfacing member may alternatively include a configuration of any of the previously described embodiments to retain the container and that steps S1101 and S1104 of FIG. 11A may be substituted with steps S1201 and S1204 of FIG. 11B in some embodiments so that the method proceeds as illustrated in FIG. 11B with steps S1202 and S1203 of FIG. 11B corresponding to steps S1102 and S1103 of FIG. 11A. The interfacing member may remain mated to the syringe when the syringe is in use. The interfacing member may non-detachably mate with the container such that the container may not be easily removed after mating. Alternatively, the interfacing member may detachably mate with the container such that the container may be removed and reattached, for example, when additional medication is to be drawn up. In such cases, a tether may be used to retain a connection between the syringe and the container, even when the container is detached. The container may be mated to the interfacing member such that the label of the container is visible and the contents of the syringe are readily identifiable from the label.

Figure 11C:
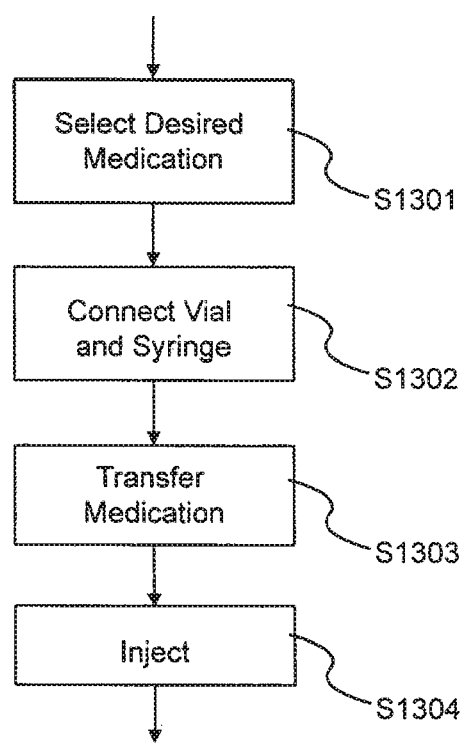
FIG. 11C illustrates another method for labeling a syringe according to an exemplary embodiment of the present invention.

According to another exemplary embodiment of the present invention, the method of use follows the sequence shown in FIG. 11C. First, the desired medication is selected (Step S1301). Then, the vial may be connected to the syringe (Step S1302). Then, the medication may be transferred from the vial to the syringe while the vial is in a connected state (Step S1303). Medication may then be injected (Step S1304).

Accordingly, when one or more of the exemplary embodiments are performed, the syringe may be labeled independently of practitioner input.

According to exemplary embodiments of the present invention, the interfacing member may be a casing or bag member attached to the syringe. The casing or bag member may be either flexible or rigid and may contain a closing means such as a cap, draw string, twist tie, and/or zip lock. The casing or bag member may be transparent or may have at least a transparent window. Thus, a medication container may be placed in the casing or bag member when not in use, and a label of the container may be seen through the casing or bag member.

Figure 12:
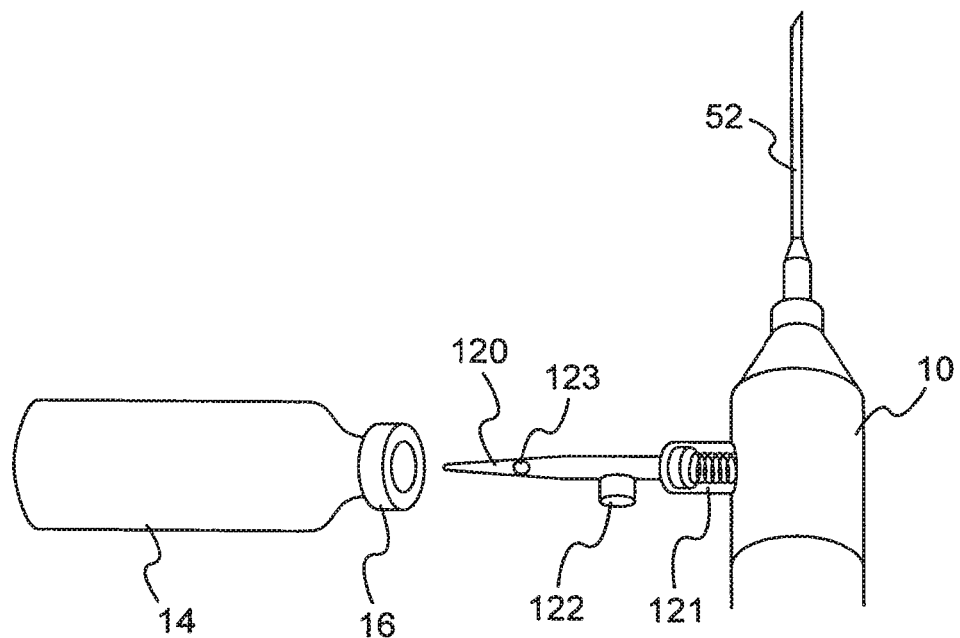
FIG. 12 is a schematic illustrating a syringe capable of mating with a medicine container and drawing medication from the container while in a mated state according to an exemplary embodiment of the present invention.

Exemplary embodiments of the present invention may allow for the communication of medication from the container to the syringe while the container is mated to the syringe. Such exemplary embodiments may therefore minimize the risk of mislabeling by maintaining a mated state of the container with the syringe, while allowing for simplified drawing of medication from the container to the syringe. FIG. 12 is a schematic illustrating a syringe capable of mating with a medicine container and drawing medication from the container while in a mated state according to an exemplary embodiment of the present invention.

The syringe 10 may include a filling needle 120 and a needle-mount 121. The filling needle 120 may be inserted into the container 14. The filling needle 120 may include an air vent 122 for releasing air that is drawn from the container 14 so that air is not drawn into the syringe 10. The needle-mount 121 may include a one-way valve to prevent fluid in the syringe 10 from reentering the container 14. The one-way valve may include, for example, a spring and stopper arrangement as shown. A filling hole 123 may be located on the tip of the filling needle 120 or along the side of the filling needle 120 to facilitate the drawing of medication as the volume of medication in the container 14 becomes low.

According to some exemplary embodiments of the present invention, the one-way valve may be replaced with a mechanism for selectively cutting off the fluid connection between the filling needle and the syringe. For example, a switch may be used to close the fluid connection. The switch may be implemented, for example, by rotating or folding down the filling needle, or by including a dam-like separator between the chamber of the syringe 10 and the filling needle 120, which can be selectively opened or closed.

When the filling needle 120 is inserted into the container 14, the container 14 may be clearly visible to allow for the label of the container 14 to serve as a label for the syringe 10 and to clearly identify the contents of the syringe. The container 14 may be held in place by the friction of the filling needle 120 within the container 14, or a receiving element (not shown) may be provided on the filling needle 120 or needle-mount 121 to receive the cap 16 of the container 14 and provide added support.

A medical practitioner, having inserted the filling needle 120 into the container 14 may then draw medication from the container 14 via the filling needle 120. To prevent air from being drawn into the syringe 10 via the hypodermic needle 52, a one way valve may be incorporated into the syringe 10 or hypodermic needle 52. Any air drawn from the container 14 may be released from the air vent 122. Alternatively, a selectable valve mechanism may be used to allow the medical practitioner to choose whether medication is to be drawn from the filling needle 120 or the hypodermic needle 52.

Figure 13:
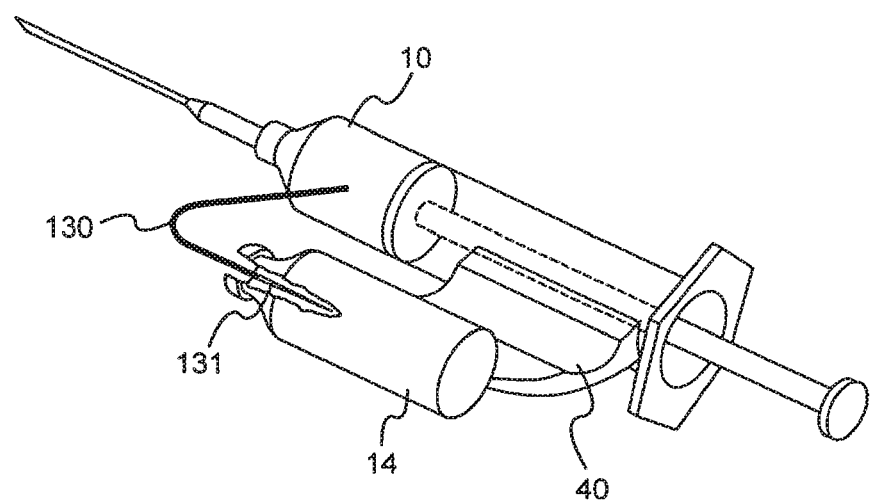
FIG. 13 is a schematic illustrating a syringe capable of mating with a container and drawing medication from the container while in a mated state according to an exemplary embodiment of the present invention.

Exemplary embodiments of the present invention may allow for fluid communication between the container and the syringe without relying on the filling needle to hold the container in place. FIG. 13 is a schematic illustrating a syringe capable of mating with a container and drawing medication from the container while in a mated state according to an exemplary embodiment of the present invention. Here, the container 14 may be mated to the syringe 10, for example, by using one of the techniques and/or apparatuses described above and illustrated in the figures. For example, an adhesive cup 40, as described above, may be used as an interfacing member to mate the container 14 to the syringe 10. A filling needle 131 may be provided at the end of a filling tube 130. The filling tube 130 may be rigid or flexible, however, a flexible filling tube may more easily allow for the insertion of the filling needle 131 and the mating of the container 14 to the adhesive cup 40. The filling tube 130 may also serve as a tether as described above. A one way valve (not shown) may be used for preventing medication from being pushed into the container 14 and an air vent (not shown) may be used to vent air drawn from the container 14).

As is seen in FIG. 12, exemplary embodiments of the present invention including a filling needle 120 may provide the filling needle 120 perpendicularly to the hypodermic needle 52. Alternatively, the filling needle 120 may be provided antiparallel to the hypodermic needle, as seen, for example, in FIG. 14.

Figure 14:
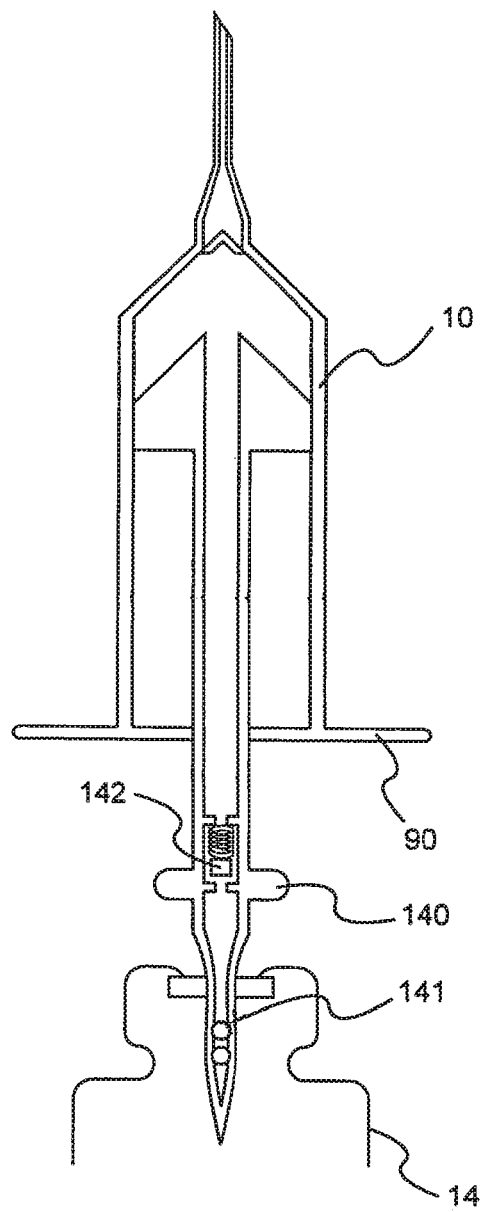
FIG. 14 is a schematic illustrating a syringe capable of mating with a medicine container and drawing medication from the container while in a mated state according to an exemplary embodiment of the present invention.

FIG. 14 is a schematic illustrating a syringe capable of mating with a medicine container and drawing medication from the container while in a mated state according to an exemplary embodiment of the present invention. Here, a filling needle 141 is provided antiparallel to the hypodermic needle 52. The filling needle may be attached to the plunger 140 of the syringe 10, for example, such that fluid is communicated through the plunger 140. As described above, a one-way valve 142 may regulate the direction of flow though the filling needle 141 to ensure that fluid can be drawn from the container 14 but cannot be pushed from the syringe 10 back into the container 14.

Figure 18:
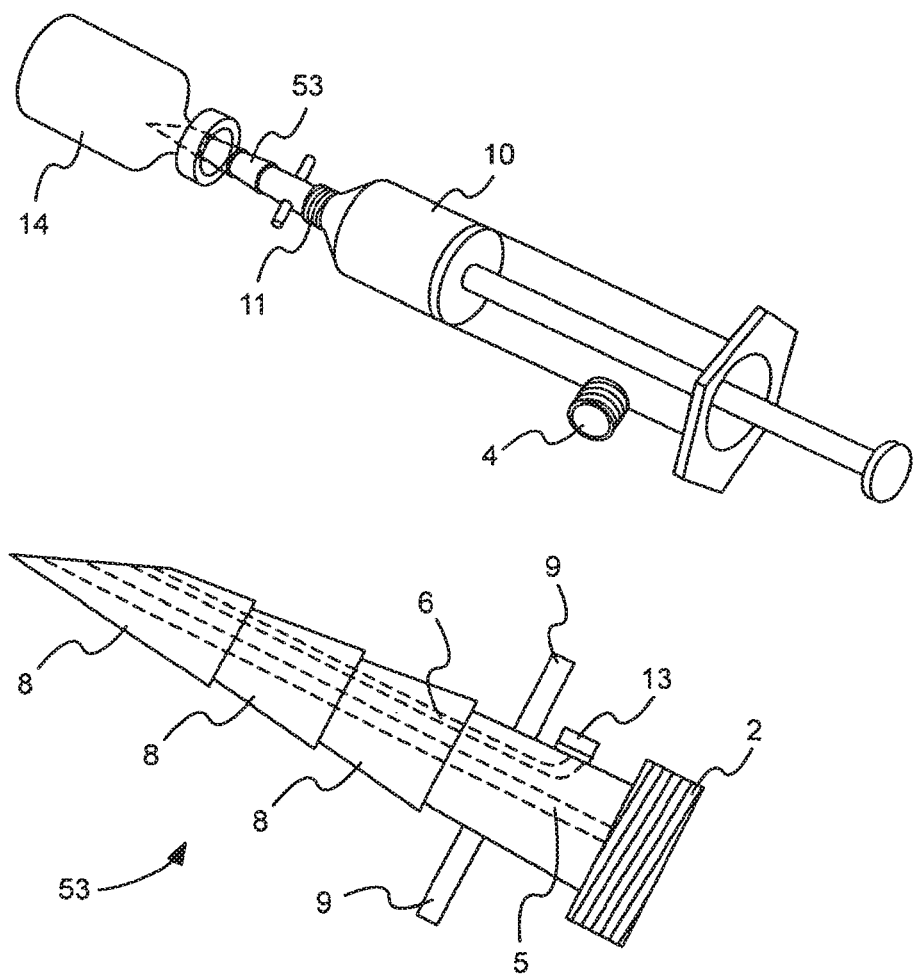
FIG. 18 is a syringe and penetration spike according to an exemplary embodiment of the present invention.

FIG. 18 is a syringe and penetration spike according to an exemplary embodiment of the present invention. The syringe 10 includes a first male leur lock connector 11 for connecting with a female leur lock of a hypodermic needle. A penetration spike 53 with a female leur lock 2 may alternatively be connected to the first male leur lock 11 of the syringe 10. Accordingly, the penetration spike 53 may be used, for example, prior to the application of the hypodermic needle to facilitate the drawing of medication from the vial 14. The penetration spike 53 may be made of metal or a hard plastic and may have a sharp tip end. The penetration spike 53 may include a series of ridges 8 for allowing the vial 14 to be easily inserted while preventing the vial 14 from being removed from the penetration spike 53. Thus, after medication has been drawn to the syringe 10 from the vial 14 through the spike 53, the spike 53, attached to the vial, may be removed from the syringe 10.

The spike 53 so removed may then be reattached to the syringe 10, for example, to a second male leur lock 4 that is positioned elsewhere on the syringe. For example, the second leur lock 4 may be located on the side of the syringe 10, as shown, or alternatively on the back of the syringe. Thus, the vial 14 may remain associated with the syringe 10 including the medication so that the contents of the syringe 10 are clearly visible by virtue of the labeled vial.

According to some exemplary embodiments, the second male leur lock 4 may function as a post for securing the spike 53 and may not allow for fluid exchange between the syringe 10 and the spike 53.

Either or both of the first male leur lock 11 and the second male leur lock 4 may be protected with a leur cap, for example, of the type discussed above and illustrated in FIGS. 17*a* and 17*b*. Alternatively, a tethered female leur cap may be used, particularly for the second male leur lock 4.

The spike 53 may include separate paths for medication withdrawal 5 and air entry 6 to displace the volume of the drawn up medication. Alternatively the spike could be non-vented, possessing only the path for medication withdrawal 5. In the embodiment with the two paths 5 and 6, drawn air entering the vent can pass through an antibacterial filter 13 prior to entering the vial.

The spike 53 may additionally include handles 9 for facilitating untwisting of the spike 53 from the syringe's first mail leur 11 and re-attaching it to the second male leur 4.

After medication is drawn up, the syringe may be attached to either a hypodermic needle or directly to an IV using the male leur 11. If additional medication needs to be drawn up, the syringe may be detached from the hypodermic needle or the IV and the spike may be transferred from the second male leur 4 back to the first male leur 11.

Figure 19:
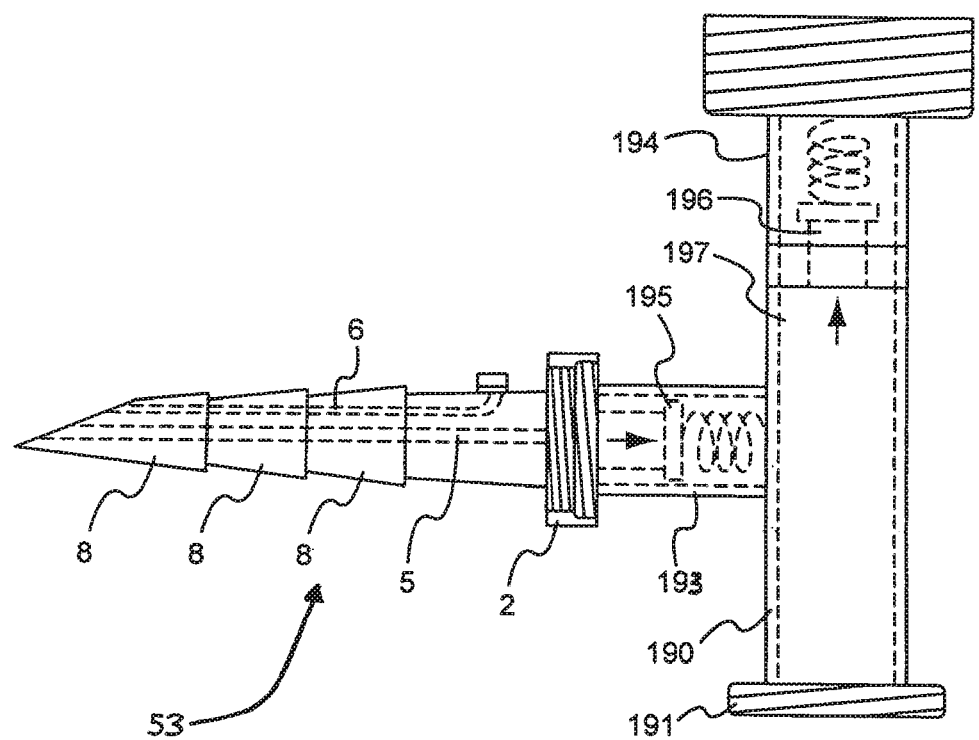
FIG. 19 is a schematic diagrams illustrating a syringe and penetration spike apparatus according to an exemplary embodiment of the present invention.

FIG. 19 is a schematic diagram illustrating a syringe and penetration spike apparatus according to an exemplary embodiment of the present invention. This exemplary embodiment is a variant of the embodiment discussed above with respect to FIG. 18, however; here, a conventional syringe may be used. Here, an adapter unit 190 has a lock 191 for attaching to the tip of a syringe. The adapter unit 190 also has a first connector 193 for connecting to a spike 53. The spike 53 may be similar to the spike described above with reference to FIG. 18. The adapter unit 190 may also have a second connector 194 for connecting to a hypodermic needle. In other exemplary embodiments, the adapter unit 190 may be integrated with the syringe, in which case no lock 191 is needed.

The first connector may include a first valve 195 that permits fluid to be drawn from the spike 53 to a body portion 197 of the adapter unit 190 and to the syringe while preventing fluid from flowing back from the syringe to the spike. The second connector 194 may include a second valve 196 that permits fluid to exit the syringe through the hypodermic needle while preventing fluid from flowing back from the needle to the syringe. Accordingly, the vial may remain attached to the spike which may remain attached to the syringe so that the contents of the syringe may be known. Moreover, additional medication may be easily drawn without having to remove the spike. In this embodiment, handles 9 may be omitted from the spike 53 as the spike need not be repeatedly removed and reattached. Additionally, the second connector 194 may attach directly to an IV where no hypodermic needle is desired.

As described above, the adapter unit 190 may be separate from the syringe or may be integrated with the syringe. For example, the adapter unit 190 may be permanently attached to the syringe.

The above devices may be used as part of an intravenous anesthesia machine and may be combined with a bar code scanner, as described above, to identify the medication in the vial. The intravenous anesthesia machine may include an optical sensor for keeping track of the volume of medication injected. Alternatively, a video capture device may be used to identify the contents of the vial by performing optical character recognition on the vial label or by pattern recognition system in accordance with known methods for computer vision-based identification. Drug identification may also be confirmed verbally by means of a computer program that speaks the name, concentration and starting volume or total dose in the syringe prior to giving any medication.

Figure 15:
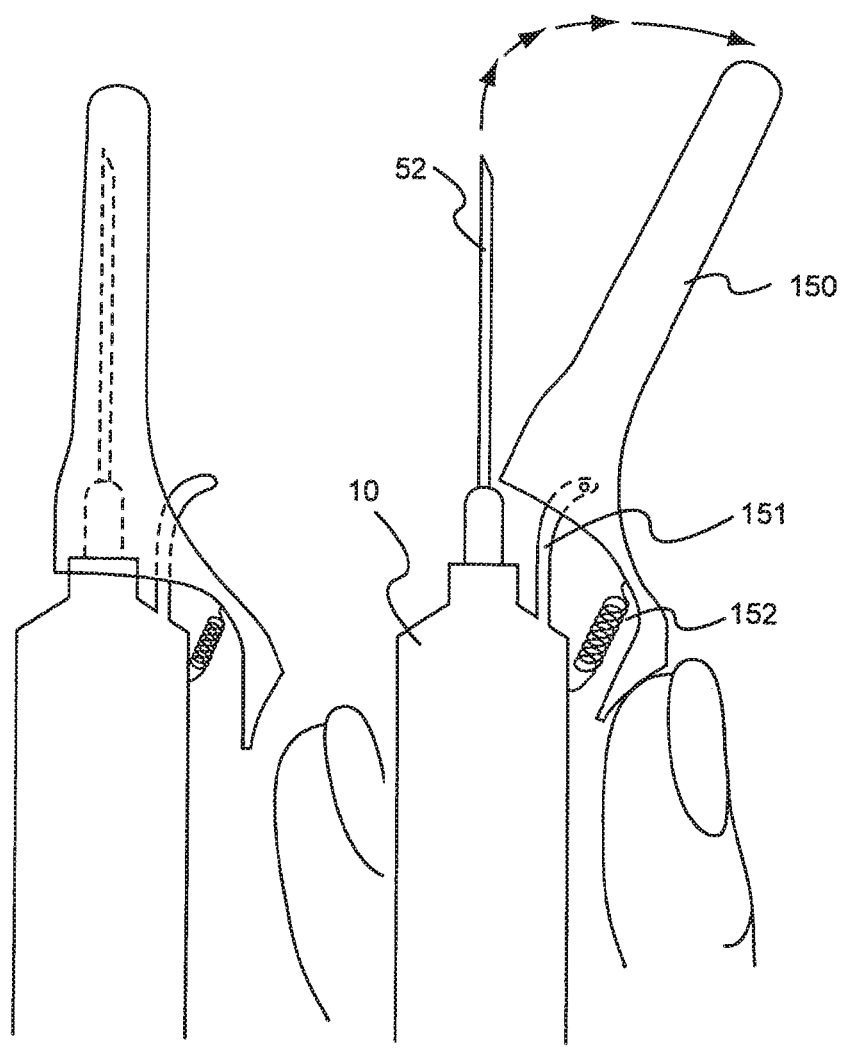
FIG. 15 is a schematic illustrating a spring-loaded needle sheath according to an exemplary embodiment of the present invention.

Exemplary embodiments of the present invention may also provide for a spring-loaded needle sheath for covering the hypodermic needle when not in use. FIG. 15 is a schematic illustrating a spring-loaded needle sheath according to an exemplary embodiment of the present invention. Covering a hypodermic needle 52 allows for the syringe 10 to be placed down without risk of contaminating the needle 52. Exemplary embodiments of the present invention allow for the single-handed covering of the hypodermic needle in such a way that the practitioner would not have to hold the syringe in one hand and the separate cap in the other hand, and place the cap on the needle, an action that may present an increased risk of puncture injury.

Accordingly, exemplary embodiments of the present invention endeavor to sheath the hypodermic needle without risk of accidental puncture. Accordingly, exemplary embodiments of the present invention provide for a needle sheath 150 that protects the hypodermic needle 52 when not in use. The sheath 150 may have a cutout (not shown) that is larger than the needle so that the sheath may be easily pulled from and returned to the needle 52 without obstruction. The sheath 150 may be connected to a pivot 151 and may be spring-loaded with a spring 152. The configuration of sheath 150, pivot 151, and spring 152 are provided as an example and other arrangements are possible.

The sheath 150 may be arranged such that it tends to a closed position in the absence of force. Accordingly, when the hypodermic needle 10 is put down or dropped, the sheath 150 quickly covers the needle such that risks of contamination and/or accidental puncture are reduced.

Figure 16:
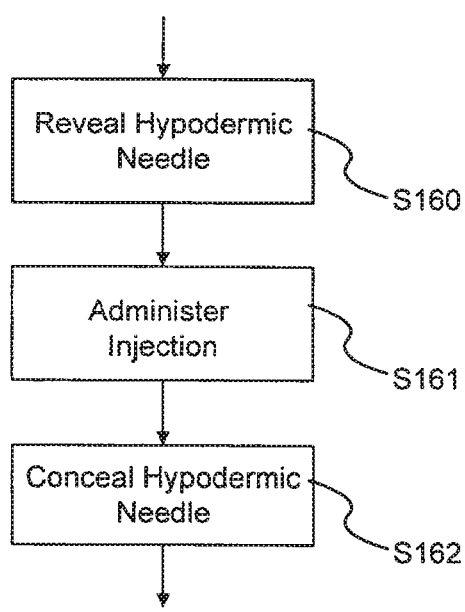
FIG. 16 is a flow chart illustrating a method for administering a hypodermic injection according to an exemplary embodiment of the present invention.

FIG. 16 is a flow chart illustrating a method for administering a hypodermic injection according to an exemplary embodiment of the present invention. First, force may be applied to the needle sheath to move, for example, slide and/or rotate, the sheath around pivot 151 and reveal the hypodermic needle (Step S160). Then, while the needle is revealed, and while force continues to be applied, the hypodermic injection may be administered (Step S161). Finally, after the injection has been administered, the force may be discontinued and the needle sheath may return to its original position concealing the hypodermic needle (Step S162).

Figures 17A, 17B:
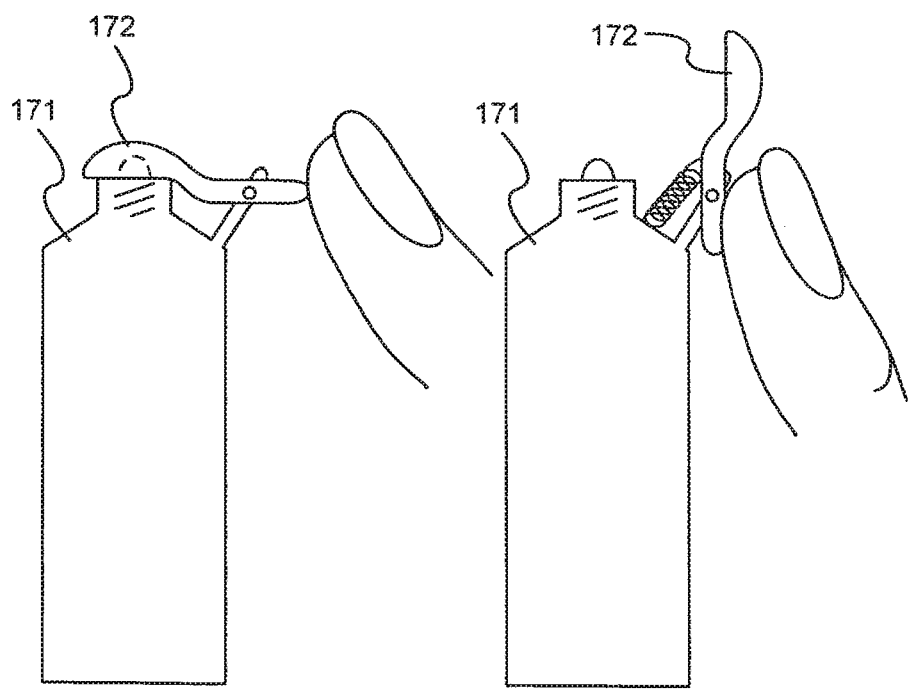
FIGS. 17a and 17b are schematics illustrating a luer tip syringe with a protective cap according to an exemplary embodiment of the present invention.

FIGS. 17a and 17b are schematics illustrating a luer tip syringe with a protective cap according to an exemplary embodiment of the present invention. When a hypodermic needle is not attached to a syringe, as shown in the syringe of FIG. 17a and the syringe of FIG. 17b, the syringe may have an exposed male luer tip 171. To protect the male luer tip 171 from damage and to preserve its sterility, a spring-cap 172 may be provided as part of the syringe. The spring-cap 172 may be opened with a single press such that a practitioner may both handle the syringe and open the spring-cap 172 with a single hand. The spring-cap 172 may be provided with a restoring force such that there is an inclination for the spring cap 172 to close around the male luer tip 171 when an opening force is not applied. The restoring force may be provided with a spring or another restoring device such as an elastic member or a memory foam.

Exemplary embodiments of the present invention may substantially reduce or virtually eliminate the risk of mislabeling syringes that are filled with various medications. Accordingly, medication may be more safely administered to patients, for example, in an operating room setting. Therefore, the potential for complications resulting from administration of incorrect medication may be reduced and patient safety may accordingly be improved.

The above specific exemplary embodiments are illustrative, and many variations can be introduced on these embodiments without departing from the spirit of the disclosure or from the scope of the appended claims. For example, elements and/or features of different exemplary embodiments may be combined with each other and/or substituted for each other within the scope of this disclosure and appended claims.

What is claimed is:

1. A system comprising:
a penetrating spike; and
a syringe;
wherein the penetrating spike is adapted for attachment to the syringe;
wherein the penetrating spike comprises:
a body unit that at one end is adapted to be inserted into a vial; and
an adapter unit for connecting the body unit to the syringe;
wherein the adapter unit is located at a second end of the body unit opposite to the one end that is adapted to be inserted into the vial;
wherein the body unit contains one or more ridges for preventing the body unit from being removed from the vial; and
wherein the entirety of the syringe extends between a top end and a bottom end opposite the top end and comprises:
a first adapter unit at the bottom end for mating with the adapter unit of the penetrating spike; and
a second adapter unit adjacent the top end for mating with the adapter unit of the penetrating spike, wherein the second adapter unit does not allow for fluid exchange between the syringe and the penetrating spike.

2. The system of claim 1, wherein the first and second adapter units each comprise luer connectors.

3. The system of claim 2, wherein at least one of the luer connectors comprises a cap covering the at least one of the luer connectors.

4. The system of claim 3, wherein the cap is biased in a position covering the at least one of the luer connectors.

5. The system of claim 1, wherein the penetrating spike further comprises one or more handles for facilitating removal or placement of the penetrating spike from or to the syringe.

6. The system of claim 1, wherein the body unit includes a first pathway for passing fluid from the vial to the syringe and a second pathway for allowing air to enter the vial as the fluid is removed.

7. The system of claim 1, wherein:
the syringe comprises a cylindrical body having a height extending between the top end to the bottom end; and
the second adapter unit is positioned on a surface of the cylindrical body.

8. The system of claim 7, wherein the second adapter unit contacts the surface of the cylindrical body.

9. The system of claim 1, wherein the one or more ridges comprise a plurality of ridges in a stacked configuration.

10. A system comprising:
a penetrating spike; and
a syringe;
wherein the penetrating spike is adapted for attachment to the syringe;
wherein the penetrating spike comprises:
a body unit that at one end is adapted to be inserted into a vial; and
an adapter unit for connecting the body unit to the syringe;
wherein the adapter unit is located at a second end of the body unit opposite to the one end that is adapted to be inserted into the vial;
wherein the body unit contains one or more ridges for preventing the body unit from being removed from the vial; and
wherein the entirety of the syringe extends between a top end and a bottom end and comprises:
a first adapter unit for mating with the adapter unit of the penetrating spike, wherein the first adapter unit is located at the bottom end of the syringe;

a second adapter unit spaced apart from the first adapter unit for mating with the adapter unit of the penetrating spike; and a cylindrical body having a height extending in a direction from the top end to the bottom end;

wherein the second adapter unit is positioned on a surface of the cylindrical body adjacent the top end; and wherein the second adapter unit does not allow for fluid exchange between the syringe and the penetrating spike.

11. The system of claim 10, wherein the second adapter unit contacts the surface of the cylindrical body.

12. The system of claim 10, wherein the one or more ridges comprise a plurality of ridges in a stacked configuration.

* * * * *